United States Patent [19]

Carano et al.

[11] Patent Number: 5,785,520
[45] Date of Patent: Jul. 28, 1998

[54] ORTHODONTIC DISTALIZING APPARATUS

[75] Inventors: Aldo Carano, Taranto; Mauro Testa, Avigliana, both of Italy

[73] Assignee: Micerium S.R.L., Avegno, Italy

[21] Appl. No.: 643,921

[22] Filed: May 7, 1996

[51] Int. Cl.$^6$ .................................................. A61C 3/00
[52] U.S. Cl. ............................. 433/7; 433/18; 433/6
[58] Field of Search ............................ 433/6, 7, 18, 19, 433/21, 24

[56] References Cited

U.S. PATENT DOCUMENTS

| | | | |
|---|---|---|---|
| 3,293,747 | 12/1966 | Denholtz | 433/21 |
| 4,202,100 | 5/1980 | Forster | 433/7 |
| 4,571,178 | 2/1986 | Rosenberg | 433/7 X |
| 4,723,910 | 2/1988 | Keller | 433/7 |
| 5,022,855 | 6/1991 | Jeckel | 433/18 |
| 5,064,370 | 11/1991 | Jones | 433/21 |
| 5,645,422 | 7/1997 | Williams | 433/7 |

OTHER PUBLICATIONS

Dynaflex Laboratories—Series 2000 —"The Future of Orthodontics", 1996.
Dynaflex Laboratories—DMJ 2000—Distalizing Molar Jig, 1997.

*Primary Examiner*—Nicholas D. Lucchesi
*Attorney, Agent, or Firm*—Foley & Lardner

[57] ABSTRACT

An orthodontic distalizing apparatus, of the type applicable removably to a dental arch, comprises a supporting framework (1) equipped with anatomical means supporting framework equipped with an anatomical support device for supporting the framework on a part of the basal gingiva and underlying bony support of the arch, preferably on the lingual side thereof. The apparatus further comprises a device for anchoring the framework to at least one anchoring tooth and pusher elements that may be spring loaded. The pusher elements are interposed between the framework and a device for fastening to a further tooth of at least one side of the arch. The pusher elements exert a distalizing force in the direction of the longitudinal axis of the arch in the region of the tooth being distalized. The pusher elements are arranged on the lingual side of the dental arch, preferably in a position lowered toward the basal gingiva and underlying bony support of the arch. Once distalizing is complete, the pusher elements can be locked to convert the apparatus into a retention device.

17 Claims, 3 Drawing Sheets

ORTHODONTIC DISTALIZING APPARATUS

TECHNICAL FIELD

This invention relates to an orthodontic distalizing apparatus for correcting the relative position of the teeth.

BACKGROUND OF THE INVENTION

Orthodontic distalizing devices for correcting the relative position of the teeth of a dental arch are known. In such known devices of this kind, spring-loadable pusher means are generally arranged on the side opposite the lingual side of the dental arch. Moreover, the pusher means are interposed between the means for anchoring the framework to a tooth selected for that purpose and the means for fastening to the further tooth being distalized of the same branch of the dental arch. The reaction force exerted by the pusher on the tooth being distalized is not discharged completely onto the basal gingiva and underlying bony support of the arch, but can also act at least partially on the tooth selected for anchoring of the framework, thus resulting in the risk of causing displacement of the latter as well.

The pusher of the known distalizing apparatuses generally consists of a pusher pin which is fastened substantially tangentially to the tooth being distalized, and on which is mounted in coaxially sliding fashion a compression sleeve of a pusher spring. The spring is interposed between the head end of the pin, rigidly fastened to the means for fastening to the tooth being distalized, and the facing head end of the sliding sleeve. The latter is in turn joined to the anchoring means of the framework via wires or the like, with which it is held in the desired spring compression position. For this purpose the pusher pin must extend sufficiently beyond the anchoring tooth, in a direction opposite to the compression direction of the spring, as a result of which the pusher means have considerable dimensions and are thus retained non-rigidly or only in a direction opposite to the direction of spring compression on the anchoring tooth. The pusher pin therefore does not exert sufficiently precise directional guidance on the tooth to prevent the forces exerted by the pusher means from being expressed, even partially, as torques capable of causing tilting of the tooth from the correct vertical orientation and/or rotation thereof, and/or as components transverse to the gingival arch.

It is therefore the object of the invention to implement an orthodontic distalizing apparatus that, by means of a relatively simple and low-cost design, effectively eliminates the drawbacks of known devices, while at the same time offering better functional performance and greater practicality.

SUMMARY OF THE INVENTION

The invention achieves the aforesaid objects with an orthodontic distalizing apparatus of the type described initially, in which the pusher means are provided on the lingual side of the dental arch. Advantageously, the pusher means are implemented so as to have rigid attachment points to the means for fastening to the tooth being distalized, and to the support framework anchoring means.

An orthodontic distalizing apparatus is provided in accordance with the invention for correcting the relative position of the teeth of a dental arch. Such apparatus is of the type applicable removably to a dental arch, the apparatus comprising a supporting framework equipped with anatomical means for support on a part of the basal gingiva and underlying structures, preferably on the lingual side thereof, and means for anchoring to at least one tooth, preferably to two symmetrically opposite teeth of the said arch, as well as pusher means that can be spring loaded to the desired extent and interposed between the framework and means for fastening to a further tooth of at least one side of the said arch.

Preferably, the pusher means and/or the elements joining them to the framework and to the means for fastening to the tooth being distalized are shaped so they are arranged on the lingual side of the dental arch at the cervical margin of the tooth or in the basal zone of gingiva of the arch. The pusher means are joined on the one hand to the means for fastening to the tooth being distalized, and on the other hand directly and rigidly to the anatomical means for support of the framework on the gingival arch.

In this case it is advantageous to provide pusher means consisting of a tubular element fastened, with one end projecting in the displacement direction, to the anatomical support means, into which tubular element is inserted, coaxially and in freely slidable fashion, a pusher pin whose free end is joined rigidly to the means for fastening to the tooth being distalized, while a pusher spring is interposed between a shoulder on the said joining end of the pusher pin and a bushing which is coaxially slidable on the tubular element and is equipped with means for locking in position.

According to an improvement, the means for fastening the framework to the anchoring tooth are rigidly joined to the anatomical support means for the framework via elastic means that can be preloaded so as to compensate for the dynamic reaction forces that may be discharged on the said anchoring tooth.

As a result of the aforesaid arrangements, the apparatus according to the invention has a substantially more compact design that is less irritating for the patient. Any dynamic forces on the anchoring tooth are effectively compensated for, thus preventing displacement of the latter. Rigid and precise guidance in the desired direction is created for the tooth being distalized, preventing transverse deflections, rotations, and/or inclinations thereof, all without further complicating either the configuration or the handling of the apparatus.

Other features of the invention will become apparent from the following detailed description. It should be understood, however, that the detailed description is given by way of illustration only, since various changes and modifications within the spirit and scope of the invention will become apparent to those skilled in the art from this detailed description.

BRIEF DESCRIPTION OF THE DRAWING

The particular characteristics of the invention and the advantages deriving from it will be evident in greater detail from the description of a preferred embodiment depicted as a non-limiting example in the attached drawings, in which.

DETAILED DESCRIPTION OF PREFERRED EMBODIMENTS

Figure 1:
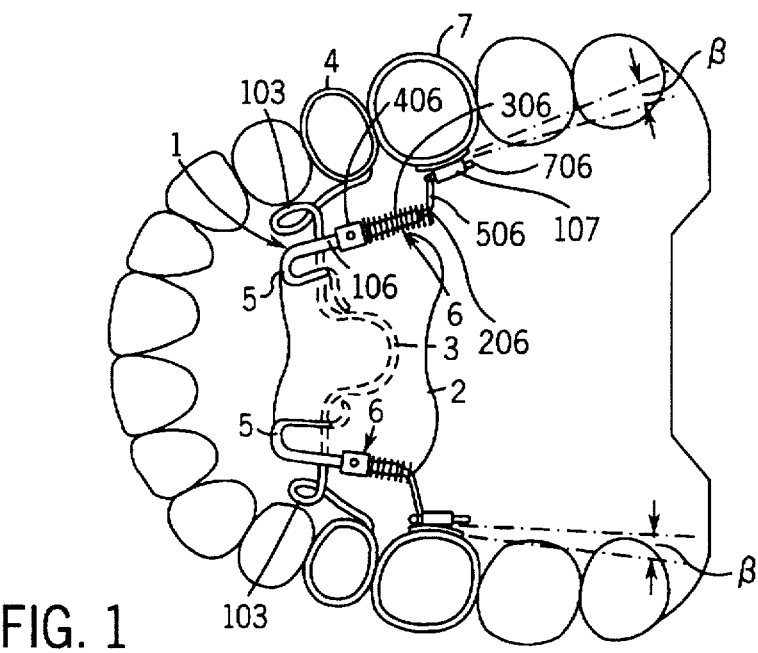
FIG. 1 depicts a top view of an apparatus according to the invention, applied to a dental arch.

Referring to the Figures, an orthodontic distalizing apparatus comprises a framework 1 composed of an element 2 for support on the median lingual side of a gingival arch, called a Nance button, proceeding from which is a first transverse structure 3 made of wires of suitable metal. Transverse structure 3 is joined at each end to respective bands 4 for anchoring to a predefined anchoring tooth. Proceeding from Nance button 2 is a second transverse structure 5, one or both of whose opposite ends are joined by means of pusher elements, labeled globally as 6, to further bands 7 for fastening to a tooth being distalized. Pushers 6 are oriented so as to exert a pushing force in the direction of the longitudinal axis of the dental arch. The attachment point of pusher means 6 to transverse structure 5 is arranged so that the pusher means extend at a level of the arch located at the lowest possible position within the basal zone of gingiva, while the attachment point of pusher means 6 to band 7 is also provided as low as possible above, or in, the cervical zone, so that it is in a position as close as possible to the resistance point of the tooth. This largely suppresses those components of the distalizing force exerted by pusher means 6 which act so as to tilt the tooth from its correct vertical orientation.

Figure 2:
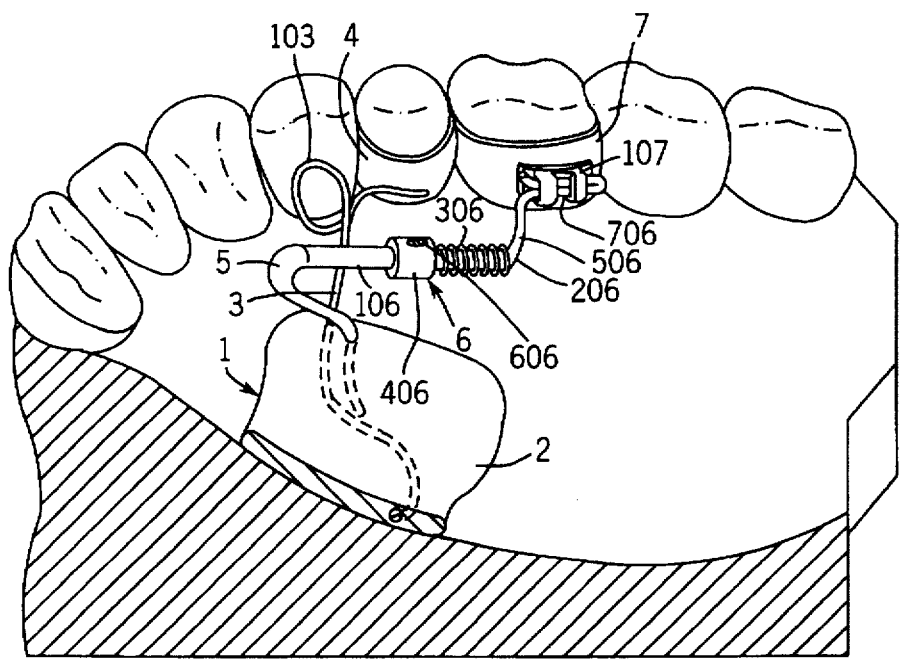
FIG. 2 depicts an enlarged lateral elevation of a detail of the device according to FIG. 1.

Transverse anchoring structure 3 has means 103 for compensating for any reaction forces which may be discharged onto the anchoring tooth. In this case the said structure has a compensation section which is suitably elastically preloaded in the direction opposite to the said reaction force components. In the example depicted (FIGS. 1 and 2 in particular), compensation means 103 consist of a loop implemented by suitably shaping the metal wire of which said structure 3 is composed, while the elastic force is supplied by the intrinsic elasticity of the said metal wire. Thus no reaction force is exerted on the anchoring tooth, and the risk of an undesired relative displacement of the said anchoring tooth is also effectively eliminated.

According to a further characteristic which is particularly effective for suppressing any rotational torques exerted on the tooth, the pusher means are fastened to band 7 with an orientation such that the distalizing force is not tangential to the tooth corresponding to the attachment point, but exhibits an angle 13 on the order of a few degrees, preferably approximately 5 degrees, toward the lingual side.

Figure 3:
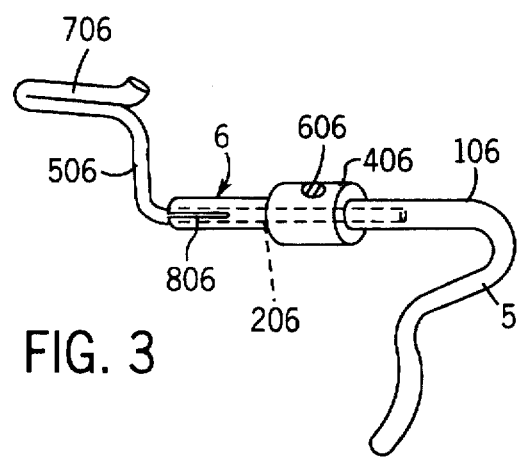
FIGS. 3 and 4 depict an enlarged detail of the pusher in two different operating states.
Figure 4:
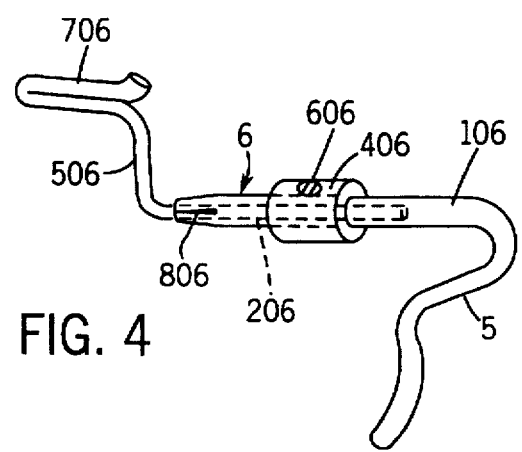

With particular reference to FIGS. 3 and 4, the pusher means consist of two parts 106, 206, telescopically engaged with one another, between which is interposed an elastic element 306 that can be preloaded as desired by a miniature bushing 406. Fastened to the ends of transverse structure 5 which discharges reaction forces is a narrow tube 106 which is oriented in the direction of the distalizing force being applied, and which extends in a low position at the level of the basal gingiva of the arch. Engaged in narrow tube 106 in a freely sliding manner, coaxially with respect thereto, is a pusher pin 206 which has at its free end, outside narrow tube 106, a radial shoulder 506. A helical spring 306 is mounted slidingly and coaxially on narrow tube 106 between said radial shoulder 506 and miniature bushing 406. Miniature bushing 406 is equipped with means for locking in position, which in the example consist of a radial screw 606 engaged in a threaded hole of the latter. The spring is loaded by simply compressing it with the aid of miniature bushing 406, and the loaded state is maintained by locking the miniature bushing on narrow tube 106 with radial screw 606.

Radial shoulder 506 of pusher pin 206 consists of a rising section which ends in the region directly above the cervical margin of the tooth with a section 706 parallel to the said pin 206, and which constitutes the end at which pin 206 is fastened to band 7. Advantageously, fastening is accomplished, in a manner known in the art, by means of a lingual tube 107 integral with said band 7 and suitably positioned, while the said terminal section 706 is suitably shaped to engage in the said lingual tube 107.

According to a further characteristic (not depicted), the Nance button can be implemented in two parts separated from one another along an anterior-posterior axis, the said two parts being interconnected via adjustable spreading means, for example an eccentric cam or the like actuatable by means of a screw, or simply a conical screw, lesser or greater threading of which into button 2 causes transverse spreading thereof. It is also possible to implement the Nance button in several parts, for example at least three, one of which is a non-spreadable support retained on transverse anchoring structure 3, and on which are mounted, so as to spread apart transversely with respect to one another, two further button parts, between which are interposed the mutual transverse spreading means thereof, only one of the branches of transverse structure 5 which carries pusher means 6 being restrained on each part. This would make it possible to limit the transverse displacement effect on the teeth being distalized, and moreover also to be able to exert transverse distalization on only one of the two opposing teeth, locking one of the two movable parts of the button to the part integral with the transverse anchoring structure.

A further advantageous characteristic of the apparatus according to the invention provides for the two telescopically connected parts 106, 206 of the pusher means 6 also to be lockable rigidly in position with respect to one another, in terms of mutual sliding. This makes it possible to use the distalizing apparatus as an anchoring structure once distalizing has been successfully completed and when it is necessary to move the further anterior teeth in the same direction, toward the distalized teeth. In this case the distalized teeth are effectively held in position in a locked state by the apparatus consisting of button 2, transverse structure 5, and pushers 6, while it is possible to apply, between the latter and any anterior tooth of the same row, means for pulling the front tooth against the previously distalized tooth which is used as an anchoring element, with no possibility for the latter to be displaced again by reaction.

In the example depicted, in order to allow narrow tube 106 and pusher pin 206 to be locked in relative position, said narrow tube 106 has an axial notch 806 in the region of its free end, by means of which it can be clamped against pusher pin 206 (see FIGS. 3 and 4). The operation is extremely simple and can be performed without having to remove the apparatus. Just as simply, it is possible to provide for recovery of spring 306 and optionally of miniature loading bushing 406, by releasing pusher pin 206 from lingual tube 107, extracting it from narrow tube 106, removing spring 306 and bushing 406, and replacing pusher pin 206, as well as clamping narrow tube 106 against the latter with pliers. A further advantage consists in the fact that with this arrangement, narrow tube 106 can also be reused simply by re-enlarging the compressed end in the region of axial notch 806, for example using suitable spreading or reaming tools.

The distalizing apparatus according to the invention can be applied equally and with suitable anatomical adaptations to both the lower and upper dental arch. Moreover, instead of bands 7 it is also possible to use bases united lingually to the tooth itself by means of an adhesive compound and a support linkage connected to the vestibular part of the tooth where there is an attachment which links it.

The invention also provides the distalizing apparatus in the form of an installation box or kit, comprising, separately or by combining all or some of them, the following elements: support framework 1 comprising compensation elements 103 of transverse structure 3, transverse structure 5, and Nance button 2; anchoring and fastening bands 4, 7; lingual tubes 107; and pusher means 6 comprising narrow tube 106, pusher pin 206, spring 306, and spring compression bushing 406. Of course, the invention is not limited to the embodiments just described and depicted, but may be extensively varied and modified, especially in terms of design, without abandoning the informing principle set forth above and claimed hereinafter.

The appliance of the invention is simple for the doctor and the patient, versatile, and reliable in terms of controlling displacement of the first and second molars. It quickly achieves the desired displacement, is easy for the patient to clean, and is not irritating or cumbersome, but most of all it can achieve final integral displacement of the upper molars.

Figure 5:
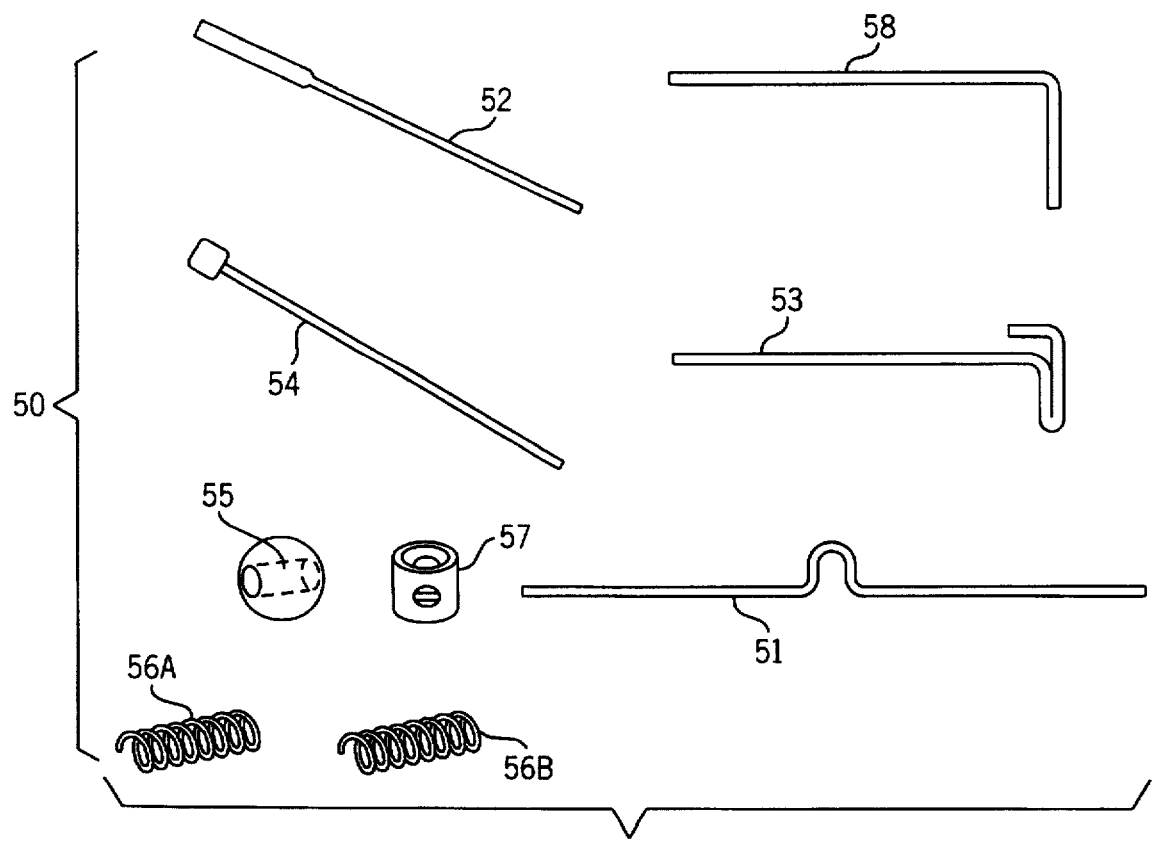
FIG. 5 depicts a kit according to the invention.
Figure 6:
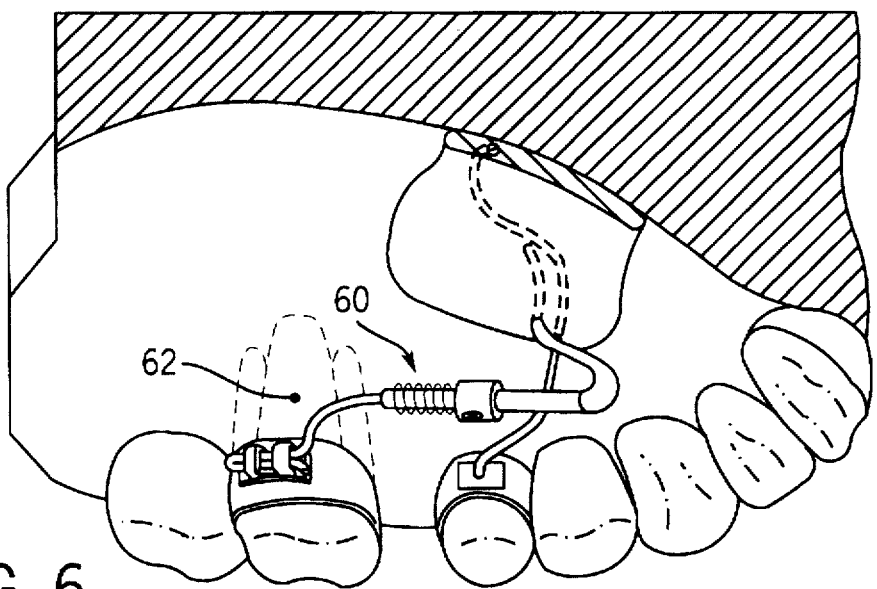
FIGS. 6 and 7 show the use of the kit of FIG. 5 in two different operating states.
Figure 7:
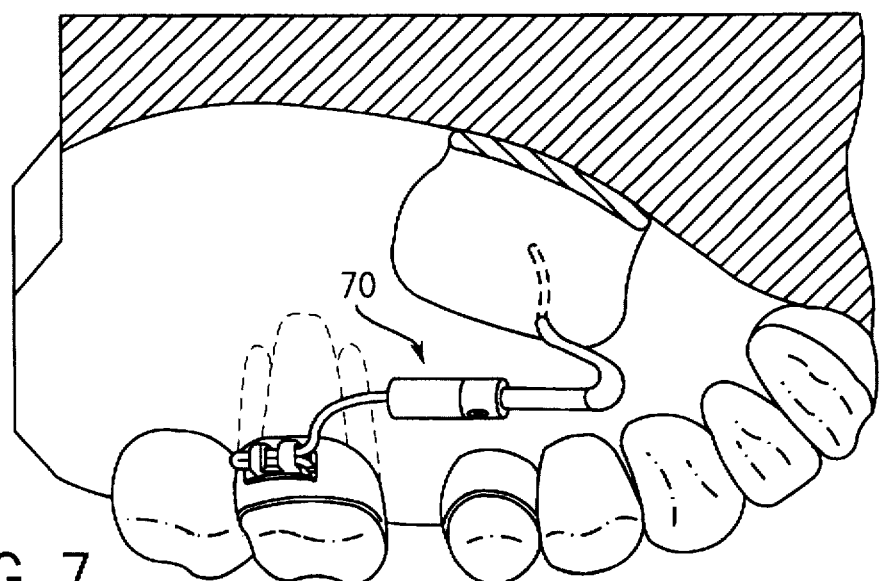

FIGS. 5 to 7 illustrate a further embodiment of a kit 50 for installing the orthodontic appliance according to the invention. Kit 50 contains: a transpremolar bar 51 which rigidly immobilizes the premolars and provides a convenient support for the palatal button; a lingual cannula 52, the interior of which supports the lingual section, while its outside diameter supports the spring and the activation screw; a molar bayonet 53, i.e., the part of the device that is drawn out of the cannula during distalization and is inserted into the lingual tube; an adhesive lingual support 54 including an adhesive premolar bonding pad 56 which can function as an optional replacement for the premolar bands and join the premolar to the palatal button; a lingual stop 55 (a plastic bead with a tranverse through hole) that prevents the spring, while it is being activated and during the time it remains compressed, from riding up on the vertical arm of the lingual section, which would cause it to operate improperly; nickel-titanium springs 56A, 56B, available in 180-gram or 240-gram versions; activation screws 57 that compress and activate the spring in one simple operation; and an activation key 58. If key 58 fits improperly, the end portion can be cut off.

Kit 50 is used as follows in a dental office installation. The modified Nance button is applied with the bands on the premolars or with the adhesive lingual support 54. The molar bayonet 53 is inserted into the lingual tube placed on the band. Insertion of the molar bayonet 53 should be checked. Bayonet 53 should be attached to the band into the lingual cannula 52 without the spring 56A or 56B and with the activation screw 57 threaded onto the lingual cannula 52. The bands on the molars should then be checked. If the bands fit correctly, the molar bayonet 53 is slid out of the lingual cannula 52, and the nickel-titanium spring 56A or 56B is inserted onto the lingual cannula 52 making sure it does not fall into the mouth. Cement is then placed in the band and the molar bayonet 53 is reinserted into the band's lingual tube. The band is then cemented onto the tooth. Spring 56A or 56B is then activated by displacing activation screw 57 distally.

Tables 1 and 2 below indicate the force exerted by the two sizes of nickel-titanium springs:

TABLE 1

| Spring 56A (240 g, .014 × .055) | | | | | | | |
|---|---|---|---|---|---|---|---|
| Compression (mm) | 1 | 2 | 3 | 4 | 5 | 6 | 7 (max. compression) |
| Loading force | 32 | 62 | 101 | 140 | 172 | 205 | 240 |
| Unloading force | 21 | 55 | 90 | 125 | 158 | 195 | — |

TABLE 2

| Spring 56B (180 g, .012 × .055) | | | | | | | |
|---|---|---|---|---|---|---|---|
| Compression (mm) | 1 | 2 | 3 | 4 | 5 | 6 | 7 (max. compression) |
| Loading force | 20 | 40 | 62 | 76 | 105 | 126 | 180 |
| Unloading force | 17 | 33 | 52 | 69 | 94 | 115 | — |

All forces are indicated in grams, and all tests were performed at a temperature of 37.7° C. A precalibrated 150-g spring should be used in mixed dentition, and a 250-g spring should be used if second molars are already present. The spring activation procedure should be repeated every month.

Once the first and second upper molars have been simultaneously distalized by an appliance 60 made using kit 50 according to the invention (FIG. 6), the distalization appliance can be converted into a molar retainer 70 by immobilizing the clamp and the spring with cold-setting or photo-activated resin and cutting the Nance arms attaching it to the premolars (FIG. 7). This converts the appliance into a Nance anchored to the molars. As shown in FIG. 6, distalization occurs integrally because the force action line passes close to the molar's resistance center 62. Once distalization is complete, as shown in FIG. 7, the appliance can easily be converted into a spacer by removing the anchoring arm on the premolar and immobilizing the active component with cold-setting resin.

In clinical installations, the following procedure should be used. Essential requirements for such an installation include: (a) a position impression with the bands in situ, which allows better positioning of the device (this in turn improves adhesion of the palatal button, which is absolutely essential); and (b) an accurate and complete impression, especially of the area of the palate where the button will be located. Once cementing is complete, adhesion and alignment of the device, particularly the button, must also be checked.

Installation for this embodiment is carried out as follows. Having received the position impression from the clinic, the first operation is to fit the transpremolar bar or adhesive mesh, making sure the wires are at least 1 mm away from the palate and do not interfere with occlusion of opposing teeth. The transpremolar bar is then mounted. The lingual tube is put in place to indicate the point at which the resistance center is probably located, and a pair of pliers is selected with which to bend the wire approximately as necessary. The wire is then positioned in the lingual tube, and the disto-mesial section is checked to be sure that its vertical section follows the contour of the palate, thus preventing decubitus in this arch during distalizing. The lingual sections must follow the centers of force as seen from the occlusal side and remain parallel to them; mesially they must be sufficiently short not to cross the transpremolar bar. The cannulas that will now be installed on top must meet the same requirements, and must therefore be cut if they are too long.

To maximize the distalizing capabilities of the device and provide sufficient rigidity during retention, use of the longest possible cannulas is recommended to allow for an equally long lingual section. To keep from overlapping the wires in the mesial portion, we recommend routing the occlusal arm of the transpremolar bar to the center of the canine. This will also allow for more convenient and correct positioning of the cannulas, which will follow the occlusal course of the suici, preventing unwanted derotation or expansion during distalization.

The button is an essential element of the device since its function is to absorb countermovement. It is preferably in the shape of an inverted heart, and will be delimited mesially by the distal section of the incisive papilla, which will never be touched, and laterally will run parallel to the lingual cannulas, ending distally in the mesial joining region of the two arcs. The button must also not interfere with the tongue or with the patient's speech; it is therefore absolutely necessary to make it not thick, even when an expansion screw needs to be added to it. The premolar bands can be placed on either the first or the second premolar.

It will be understood that the foregoing description is of preferred exemplary embodiments of the invention, and that the invention is not limited to the specific forms shown. Modifications may be made in the preferred embodiment without departing from the scope of the invention as expressed in the appended claims.

We claim:

1. Orthodontic distalizing apparatus of a type applicable removably to a dental arch for correcting the relative position of teeth of the dental arch, the apparatus comprising:
   a supporting framework equipped with anatomical support means for supporting the framework on a part of basal gingiva and underlying bony support of the arch;
   means for anchoring the framework to at least one anchoring tooth; and
   pusher means interposed between the framework and means for fastening to a further tooth of at least one side of the arch for exerting a distalizing force in a region of the further tooth being distalized, wherein the force is exerted in a direction of a longitudinal axis of the arch at a level of the basal gingiva, and wherein the pusher means is provided on a lingual side of the dental arch.

2. Apparatus according to claim 1, wherein the pusher means have rigid attachment points to the means for fastening to the further tooth being distalized, and to at least one of the framework and the support means thereof.

3. Apparatus according to claim 2, wherein the pusher means are joined to the framework in a position such that, with the apparatus installed, the pusher means extends at the level of the basal gingiva.

4. Apparatus according to claim 1, wherein the pusher means have a point of attachment for attaching to the tooth being distalized located in a lingual region proximate to a cervical margin of the tooth being distalized.

5. Apparatus according to claim 1, wherein the pusher means are oriented so as to exert the distalizing force with a direction deflected angularly by approximately 5 degrees in a lingual direction with respect to a tangent to the further tooth being distalized, on an attachment point on the further tooth in a mesial direction.

6. Apparatus according to claim 1, wherein the means for anchoring the supporting framework are joined to the support means via elastic compensating means which are preloaded so as to compensate for components of a reaction force to the distalizing force which may be discharged onto the at least one anchoring tooth.

7. Apparatus according to claim 6, wherein the framework has a Nance button as a support means and a transverse anchoring structure which is made of wire of suitable metal and which carries at at least one free end a band for fastening to the at least one anchoring tooth, while the elastic means comprises an intermediate section of the transverse anchoring structure having a shape capable of supplying the necessary compensation force by means of the intrinsic elasticity of the material of the transverse anchoring structure.

8. Apparatus according to claim 1, wherein the pusher means consist of two elements which are mutually engaged telescopically and freely reciprocally slidable in the direction of the distalizing force, the engaged elements having two free ends being rigidly joined to the framework and to the means for fastening to the further tooth being distalized, respectively, while elastic means that are compressible in adjustable and readjustable fashion in the distalizing direction are interposed between the two elements.

9. Apparatus according to claim 8, wherein the pusher means comprise, for each tooth being distalized, a tubular element which is oriented in the direction of the distalizing force and in which is engaged in freely coaxially slidable fashion a pusher pin which is equipped with at least one radial shoulder in a region external to the tubular element, there being slid onto the tubular element a helical spring which is interposed between the at least one radial shoulder of the pusher pin and a compression bushing which is freely slidable on the tubular element and which is equipped with means for locking in position on the tubular element, the tubular element being fastened at an end opposite to the pusher pin to the framework, and the pusher pin is adapted to be fastened at a free end to the tooth being distalized.

10. Apparatus according to claim 9, wherein the compression bushing has a radial threaded hole into which can be screwed a threaded pin for clamping against the tubular element.

11. Apparatus according to claim 9, wherein the pusher pin has, external to the tubular element, a section which is oriented substantially radially with respect to the tubular element and which ends, at a cervical margin of the tooth being distalized, with a section parallel to an axis of the tubular element for fastening to the tooth being distalized.

12. Apparatus according to claim 9, wherein the tubular element and the pusher pin can be locked in any predefined mutually sliding position.

13. Apparatus according to claim 12, wherein the tubular element has an axial notch in an end adjacent the pusher pin, the notch having a transverse orifice such as to allow constriction of a terminal section of the tubular element against the pusher pin.

14. Apparatus according to claim 1, wherein the pusher means are carried by a transverse structure joined to the support means.

15. Apparatus according to claim 1, wherein the support means are made up of a palatal button comprised, at least in a region of a transverse support structure for the pusher means, of at least two parts which are separated from one another along an anterior-posterior plane of symmetry of the dental arch, the parts being displaceable transversely to the anterior-posterior plane of symmetry by way of adjustable spreading means, the transverse support structure for the pusher means being implemented in two halves, each of which is joined to a corresponding part of the support means and carries pusher means for the tooth being distalized.

16. Apparatus according to claim 1, comprising as a kit of separate parts:

materials for the fabrication of the framework;

a first and a second transverse structure for connection to the framework; and means for coupling the framework to at least one tooth being distalized, including:

a tubular element;

a pusher pin which is freely coaxially slidable within the tubular element, the pin including a radial shoulder;

a compression bushing which is freely slidable on the tubular element and which is equipped with means for locking it in position thereon;

a spring which is interposable between the radial shoulder and the compression bushing; and means for locking the pusher pin in position within the tubular elements.

17. Apparatus according to claim 1, comprising in the assembled state:

a first and a second transverse structure connected to the framework; and means for coupling the framework to at least one distalizing tooth, including:

a tubular element;

a pusher pin which is freely coaxially slidable within the tubular element, the pin including a radial shoulder;

a compression bushing which is freely slidable on the tubular element and which is equipped with means for locking in position thereon;

a spring which is interposed between the radial shoulder and the compression bushing; and means for locking the pusher pin in position within the tubular elements.

* * * * *